United States Patent [19]

Grimberg

[11] Patent Number: 5,258,183
[45] Date of Patent: Nov. 2, 1993

[54] MEDICINE BASED ON NEUTRALIZED SULPHUR DERIVATIVES

[76] Inventor: Georges S. Grimberg, 123 rue de l'Université, 75007 Paris, France

[21] Appl. No.: 918,081

[22] Filed: Jul. 24, 1992

[30] Foreign Application Priority Data

Aug. 1, 1991 [FR] France ............... 91 09792

[51] Int. Cl.$^5$ .............................. A61K 33/04
[52] U.S. Cl. .................... 424/401; 424/642; 424/702; 424/703; 424/706
[58] Field of Search ........... 424/401, 642, 702, 703, 424/706

[56] References Cited

U.S. PATENT DOCUMENTS

| | | | |
|---|---|---|---|
| 2,688,585 | 9/1954 | Wilder et al. | 424/706 |
| 3,152,046 | 10/1964 | Kapral | 424/702 |
| 4,089,945 | 5/1978 | Brinkman et al. | 424/706 |
| 4,323,558 | 4/1982 | Nelson | 424/706 |
| 4,689,223 | 8/1987 | Arias | 424/703 |
| 5,128,141 | 7/1992 | Grimberg | 424/195.1 |
| 5,151,209 | 9/1992 | McCall et al. | 424/702 |

FOREIGN PATENT DOCUMENTS 44-27286 11/1969 Japan.
1089513 11/1967 United Kingdom.

Primary Examiner—Thurman K. Page
Assistant Examiner—Amy Hulina
Attorney, Agent, or Firm—Browdy and Neimark

[57] ABSTRACT

The medicine comprises a neutralizing association of a sulphide with a yeast extract.

9 Claims, No Drawings

MEDICINE BASED ON NEUTRALIZED SULPHUR DERIVATIVES

FIELD OF THE INVENTION

The invention relates to a medicine based on neutralized sulphur derivatives.

BACKGROUND OF THE INVENTION

Sulphur is one of the main constituents of biological systems, and particularly of the human skin. Moreover, it is a part of many medicinal molecules.

The sulphur derivatives formed by $S^{--}$ and a cation, for example $Na_2S$, sodium sulphide; $K_2S$, potassium sulphide; ZnS, zinc sulphide; $Se_4S_4$, selenium sulphide, etc., have, when in an aqueous solution, a strong smell of hydrogen sulphide $H_2S$ and an alkaline pH.

However, many waters from thermal springs contain small quantities of sulphur derivatives and are used for the treatment of rhino-pharyngitis via a nose or ear lavage.

OBJECT AND SUMMARY OF THE INVENTION

The object of the new medicine of the invention is to neutralize the unpleasant odor of the above mentioned sulphur derivatives by means of yeast extract, and to provide a medicine for nose or ear lavage or for a skin application in a cream.

For example, a 400 mg/liter $Na_2S$ solution has a pH of 10.8 and a strong $H_2S$ smell. If there is added, to one liter of this solution, 5 g of a perfectly soluble yeast extract, there is obtained a pH of 7.1 and the smell is practically neutral. The yeast extract is for example a U.S.P yeast extract.

According to the invention, the medicine is made of

| | |
|---|---|
| $Na_2S. 9H_2O$ | 4 mg |
| Yeast extract | 50 mg |
| Polysorbate 80 | 10 mg |
| Neroli essential oil | 2 μl |
| 9 0/00 NaCl solution Q.S. for | 10 ml |
| pH | 7.3 |
| Smell | Neroli |

EXPERIMENTAL STUDIES

In order to prove the efficiency of the new medicine, two nasal solutes were prepared:
one solute with the yeast extract (shown in the following Table by A)

| A | |
|---|---|
| $Na_2. 9H_2O$ | 4 mg |
| Yeast extract | 50 mg |
| Polysorbate 80 | 10 mg |
| Neroli essential oil | 2 μl |
| 9 0/00 NaCl solution Q.S. for | 10 ml |
| pH | 7.3 |
| Smell | Neroli | and the other solute without yeast extract (shown in the following Table by B):

| B | |
|---|---|
| $Na_2S. 9H_2O$ | 4 mg |
| Yeast extract | 0 |
| Polysorbate 80 | 10 mg |
| Neroli essential oil | 2 μl |
| 9 0/00 NaCl solution Q.S. for | 10 ml |
| pH | 10.8 |
| Smell | Hydrogen sulfide |

It was then found that product A has a neutral pH and a pleasant smell.

As an indication and in order to study the activity of product A, this product was compared to a 9 0/00 NaCl solution of known activity and which is widely used for nasal lavage.

50 adults having a rhino-pharyngitis were divided into two groups of 25. A first group performed two lavages every day with the product A, and a second group two lavages every day with the NaCl solution. The two treatments were made during a period of three months. No other therapy was administered during this period.

| Table of the results | | |
|---|---|---|
| | Product A | NaCl sol. |
| Rhinorrhea | | |
| Improvement | 91.7% | 59.1% |
| Oedema of the mucosa | | |
| Improvement | 94.7% | 55.6% |
| Erythema of the mucosa | | |
| Improvement | 95.8% | 76% |
| Tolerance | | |
| Perfect | 76% | 72% |
| Good | 16% | 20% |

To sum up the above disclosure, it can be said that the activity of the sulphur derivatives is perfectly known but their use is very difficult in the case of a skin application, particularly because their bad smell and their pH. The medicine which is the object of the present invention is however active and perfectly tolerated. It has no smell, if not a pleasant smell, and a pH suitable for the skin.

Although the hereabove example is a solution, it is possible to present the new medicine in the form of a soluble powder, an ointment or a cream, these products being always adapted for a contact with the skin.

I claim:

1. A composition for topical application in a form selected from the group consisting of solutions, powders, ointments, and creams, said composition comprising an effective amount of sulphide compound, and a sufficient amount of yeast extract to neutralize the odor of the sulphur compound, wherein the sulphide is selected from the group consisting of sodium sulphide, potassium sulphide, zinc sulphide and selenium sulphide.

2. A composition according to claim 1 wherein the sulphide is sodium sulphide.

3. A composition according to claim 1 wherein the pH is about 7.3.

4. A composition according to claim 1 further including polysorbate 80, sodium chloride solution and Neroli oil.

5. A method for neutralizing the odor of sulfur in a topical composition in which the active ingredient is a sulphide selected from the group consisting of sodium sulphide, potassium sulphide, zinc sulphide and selenium sulphide, comprising adding to said topical composition an effective amount of yeast extract to neutralize the odor of sulfur in said composition.

6. The method according to claim 5 wherein polysorbate 80, sodium chloride solution and Neroli oil are added with said yeast extract.

7. A composition as set forth in claim 1, wherein the yeast extract is a U.S.P. yeast extract.

8. A composition as set forth in claim 4, wherein the medicine is made of:

| | |
|---|---|
| Na$_2$S, 9H$_2$O | 4 mg |
| Yeast extract | 50 mg |
| Polysorbate 80 | 10 mg |
| Neroli essential oil | 2 µl |
| 9 0/00 NaCl solution Q.S. for | 10 ml |
| pH | 7.3 |
| Smell | Neroli |

9. A composition as set forth in claim 1, wherein the sulfide is formed by S$^{--}$ anion bound to a cation.

* * * * *